US006976396B2

(12) United States Patent
Roe et al.

(10) Patent No.: US 6,976,396 B2
(45) Date of Patent: Dec. 20, 2005

(54) LOADING DEVICE FOR NON-DESTRUCTIVE INSPECTIONS OF COMPOSITE STRUCTURES

(75) Inventors: Richard D. Roe, Wichita, KS (US); Clifford F. Shaeffer, Wichita, KS (US)

(73) Assignee: The Boeing Company, Chicago, IL (US)

(*) Notice: Subject to any disclaimer, the term of this patent is extended or adjusted under 35 U.S.C. 154(b) by 53 days.

(21) Appl. No.: 10/720,717

(22) Filed: Nov. 24, 2003

(65) Prior Publication Data

US 2005/0109119 A1 May 26, 2005

(51) Int. Cl.[7] .............................................. G01N 3/02
(52) U.S. Cl. ..................................................... 73/856
(58) Field of Search ........................ 73/856, 788, 760, 73/763, 818

(56) References Cited

U.S. PATENT DOCUMENTS

| 2,760,370 | A | * | 8/1956 | Linhorst ....................... 73/813 |
| 3,527,093 | A |   | 9/1970 | Sellers |
| 3,882,719 | A | * | 5/1975 | Fletcher et al. .......... 73/862.42 |
| 5,115,681 | A |   | 5/1992 | Bouheraoua et al. |
| 5,945,607 | A | * | 8/1999 | Peppel et al. ................. 73/856 |

FOREIGN PATENT DOCUMENTS

| GB | 1 287 731 A | 9/1972 |
| JP | 55096438 | 7/1980 |

OTHER PUBLICATIONS

Hanel V. et al., "Determination of Load Condition of Standard Screws Durting Tensile Tests Using Acoustic Emission Analysis", Apr. 23,1995, 1995 IEEE Instrumentation and Measurement Technology Conference, IMTC/95, Waltham, MA.
International Search Report for PCT/US2004/033734.

* cited by examiner

Primary Examiner—Edward Lefkowitz
Assistant Examiner—Corey D. Mack
(74) Attorney, Agent, or Firm—Alston & Bird LLP

(57) ABSTRACT

There is provided a loading device for applying a load to a composite structure during a non-destructive inspection. The loading device comprises a load indicator to indicate the load applied, which is preferably a normal load, and comprises a connector attached to the load indicator to connect the loading device to a surface of the structure. A support contacts the structure to support the load indicator and the connector. The support preferably comprises a plate and three legs, wherein the load indicator is attached to the plate and the legs contact the structure. The legs may comprise protective ends for contacting the structure and may define adjustable lengths. A load applicator in mechanical communication with the connector and the load indicator applies the load to the structure, advantageously by reducing the distance between the connector and load indicator to create the load. The connector may connect to the surface of the structure defining a protrusion or to a protrusion removably adhered to the surface of the structure.

18 Claims, 3 Drawing Sheets

LOADING DEVICE FOR NON-DESTRUCTIVE INSPECTIONS OF COMPOSITE STRUCTURES

BACKGROUND OF THE INVENTION

1. Field of the Invention

The present invention is related to non-destructive inspection equipment, and more particularly, to a loading device that applies a normal load to a composite structure being non-destructively inspected.

2. Description of Related Art

Non-destructive inspection of structures involves examining a structure without harming the structure or requiring significant disassembly of the structure. Non-destructive inspection is advantageous for many applications in which a thorough inspection of the exterior and/or interior of a structure is required. For example, non-destructive inspection is commonly utilized in the aircraft industry to inspect aircraft structures for any type of internal or external damage to the structure.

Among the structures that are routinely non-destructively tested are composite structures. In this regard, composite structures are commonly used throughout industry because of their engineering qualities, design flexibility, and low weight. As such, it is frequently desirable to inspect composite structures to identify any flaws, such as cracks, voids, or porosity that could adversely affect the performance of the composite structure.

Various types of sensors may be utilized to perform non-destructive inspections. One or more sensors may move over the area of the structure to be examined, and receive data regarding the structure. For example, a pulse-echo, thru-transmission, or shear wave sensor may be utilized to obtain ultrasonic data, such as thickness gauging, detection of laminar defects and porosity, and/or detection of cracks in the structure. Resonance, pulse echo, or mechanical impedance sensors may be utilized to provide indications of voids or porosity, such as in adhesive bondlines of the structure. The data acquired by the sensors is typically processed by a processing element, and the processed data may be presented to a user via a display or stored for subsequent analysis.

Certain internal flaws are more readily detectable when the structure being inspected is loaded so that the internal flaws become more apparent to the non-destructive inspection instruments. These internal flaws may include weak bonds that will separate when loaded or may include incomplete bonds between layers that contact one another when experiencing no load but that also readily separate once loaded. An applied load can also be used to counteract a preload on the structure to improve the inspection of the structure.

Existing loading devices use various techniques to apply a load to a structure being inspected. One destructive method of applying a load is to adhesively bond a button or other feature to a surface of the structure and cutting a portion of the structure around the adhered button. An instrument pulls the button until the portion of the structure adhered to the button breaks away from the structure, such that the maximum load indicates the structural strength of the structure but leaves a hole in the structure that must be repaired.

One non-destructive method of applying a load uses electromechanical means to magnetically apply a load to a ferromagnetic layer or portion of a structure being inspected. Such methods are limited to structures that include ferromagnetic materials since a magnet is needed to engage the structure. Unfortunately, this method is generally unsuitable for composite structures since many composites do not comprise ferromagnetic materials. A further non-destructive method consists of applying a vacuum to a surface of the structure to measure surface deformation that indicates internal or external flaws. Such vacuum stress systems require a relatively large suction area, which may limit access to the surface of the structure requiring inspection. In addition, such vacuum stress systems are not able to create a suction on a surface that defines protrusions because such protrusions would compromise the seal of the suction.

Accordingly, a need exists for a loading device for conveniently applying a load to a surface of a composite structure for non-destructive inspection. A need also exists for a loading device that can apply a load to a surface of a structure that defines protrusions.

BRIEF SUMMARY OF THE INVENTION

The invention addresses the above needs and achieves other advantages by providing a loading device for applying a load, such as a normal load, to a structure during a non-destructive inspection of the structure. The loading device comprises a load indicator to indicate the load applied to the structure and may further comprise a connector attached to the load indicator for connecting the load indicator to the surface of the structure being inspected. The loading device also comprises a support for supporting the load indicator and connector. The support contacts a surface of the structure proximate the area of the structure to be inspected. A load applicator in mechanical communication with the connector, the load indicator, and/or the structure applies the load to the structure. The load improves the results of the non-destructive inspection by accentuating some internal defects in the structure.

The loading device of further embodiments of the invention comprises a support defining at least three legs that contact the structure and a plate connecting the three legs to which the load indicator is attached. In addition, the legs may comprise protective ends for contacting the surface of the structure and may define adjustable lengths. The load applicator may comprise a turnbuckle that attaches the connector to the load indicator such that the load is created by rotating the turnbuckle. The connector may also define a threaded orifice for connecting to a surface of the structure or for threading onto a protrusion removably adhered to the surface of the structure.

A method of applying a load to a surface of a structure is also provided by the present invention. The support of the loading device is positioned on the surface of the structure such that the support contacts the surface. A connector is connected to the surface of the structure and attached to a load indicator. The load indicator is supported by the support and indicates the load as the distance between the connector and the load indicator is adjusted which applies the load to the surface of the structure. Once the load has been applied, the structure may then be inspected to reveal internal defects accentuated by the load.

The method may further comprise the step of rotating a turnbuckle to adjust the distance between the connector and the load indicator. The length of the legs of the support may be adjusted to properly contact the surface of the structure. The method may also comprise alternative steps for connecting the connector to the surface of the structure.

Accordingly, a loading device and method for conveniently applying a load, such as a normal load, to a structure undergoing a non-destructive inspection are provided. The load accentuates certain internal defects such as weak bonds or separated bonds so that the defects are more apparent to a technician performing the inspection. The loading device of the present invention may also be used on surfaces of structures that comprise protrusions or do not comprise protrusions.

BRIEF DESCRIPTION OF THE SEVERAL VIEWS OF THE DRAWINGS

Figure 1:
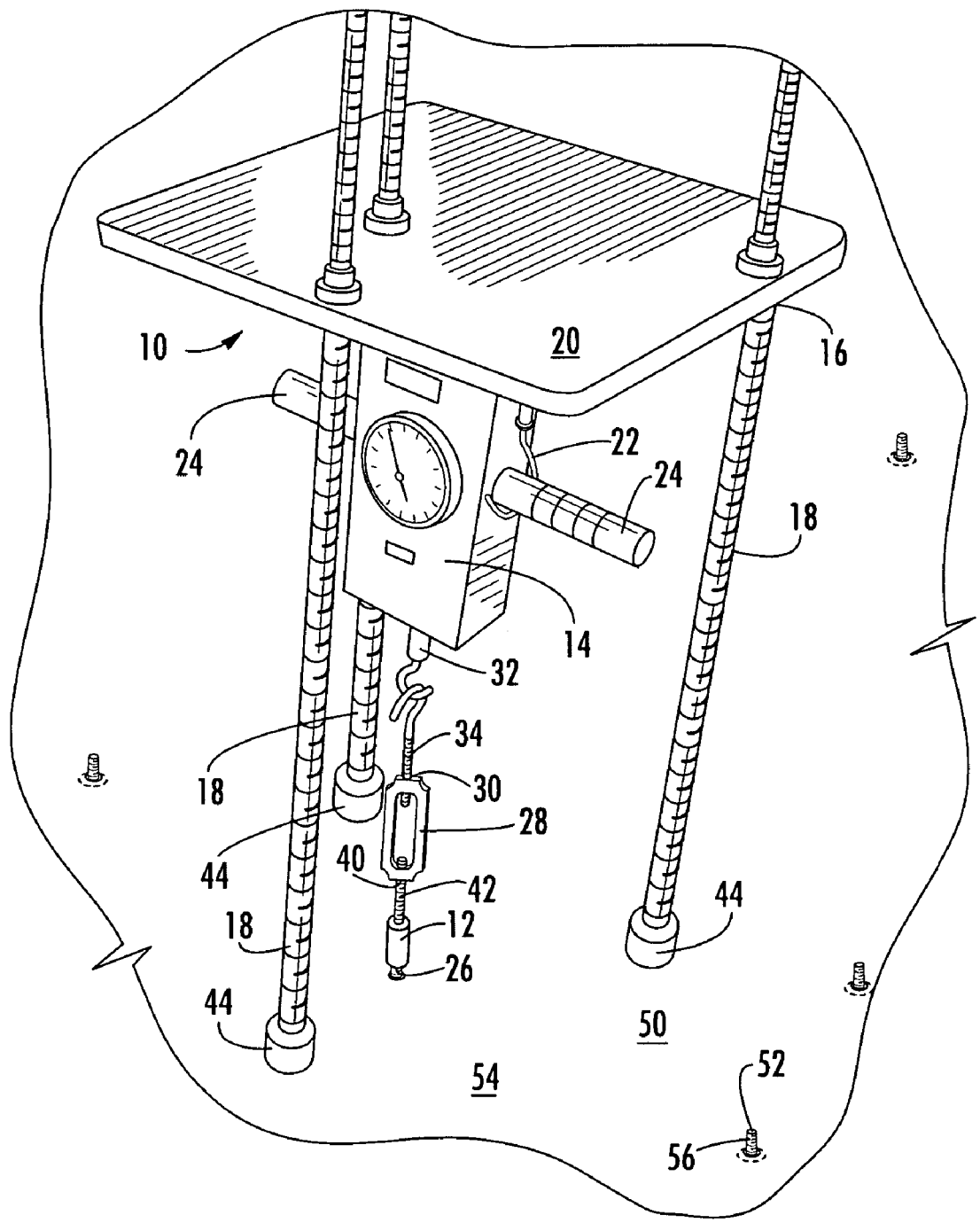
Figure 2:
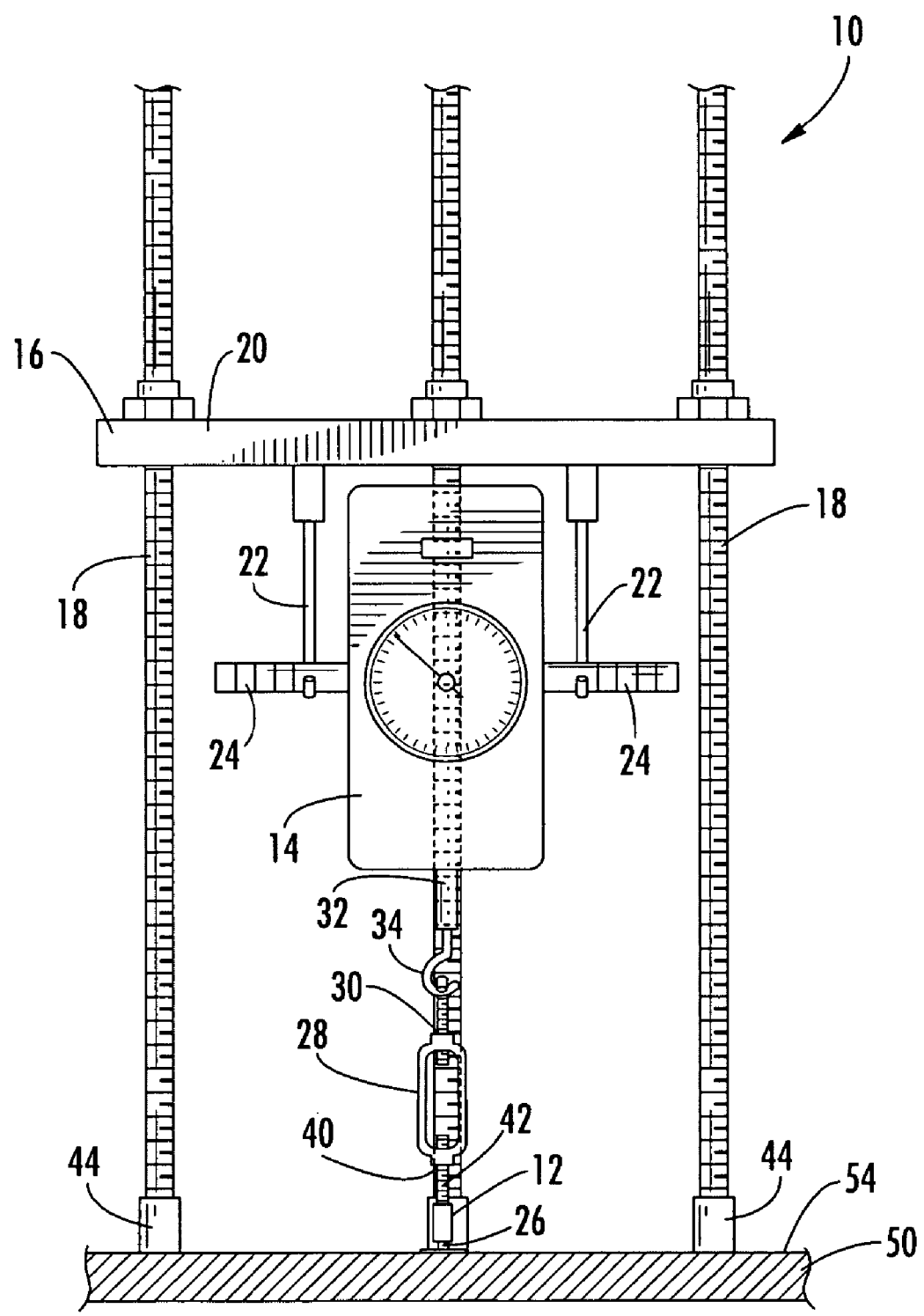
Figure 3:
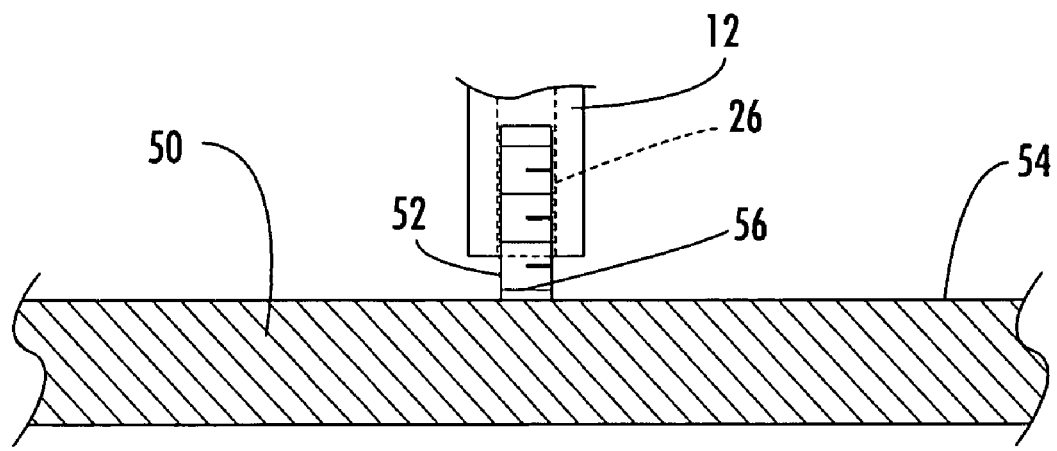
Figure 4:
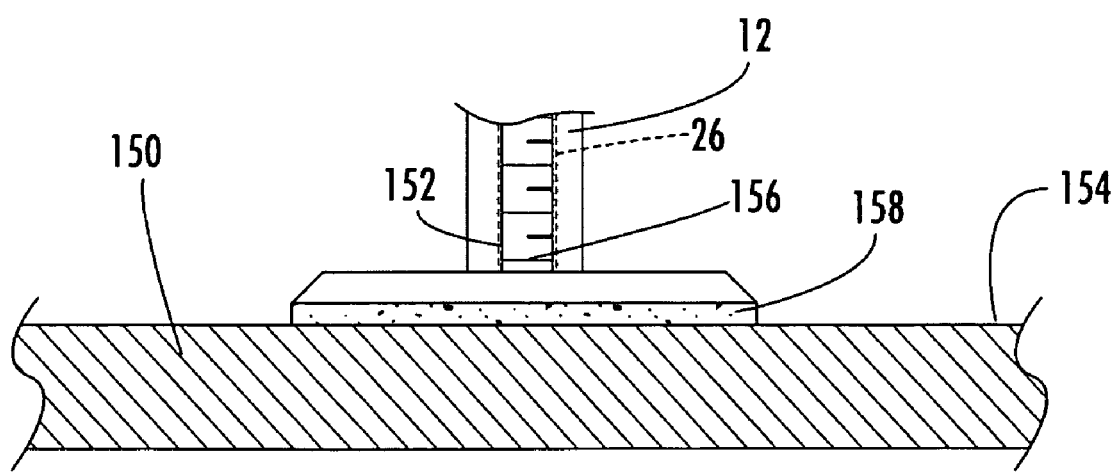

Having thus described the invention in general terms, reference will now be made to the accompanying drawings, which are not necessarily drawn to scale, and wherein:

FIG. 1 is a perspective view of a loading device in accordance with one embodiment of the present invention, illustrating the loading device connected to a protrusion from a surface of a structure to be inspected;

FIG. 2 is a front planar view of the load indicator of FIG. 1;

FIG. 3 is a front planar view of the connector of the load indicator of FIG. 1, illustrating the connection between the connector and the protrusion; and FIG. 4 is a front planar view of a connector of the load indicator of FIG. 1, illustrating the connection between the connector and a protrusion removably adhered to a surface of the structure.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1–4, a loading device 10 in accordance with one embodiment of the present invention is illustrated. The loading device 10 applies a load to a surface of a composite structure during nondestructive inspections of an area of the structure. The load applied is advantageously a normal load as in the illustrated embodiment, though further embodiments may apply a load at any direction relative to the surface of the structure. The loading device 10 of the illustrated embodiment is typically used on composite structures that may be employed in various applications, such as aerospace applications, in which the composite may include nacelle sandwich panels and engine cowls of airplanes, to list two non-limiting examples. Alternatively, the composite structures may be utilized onboard ships, automobiles, or other vehicles, or in machinery, buildings, or other structures. Further embodiments of the loading device may be used on alternative structures, including non-composite structures. The inspection procedures preferably incorporate traditional transmission ultrasound techniques with devices such as a STAVELEY BONDMASTER to list one non-limiting example. The loading device may also be used with alternative non-destructive inspection techniques or devices.

The loading device 10 of FIGS. 1–4 comprises a connector 12 for connecting the loading device to a surface of the structure being inspected. A load indicator 14 is attached to the connector 12 and comprises a dial that indicates the load applied to the structure. The load indicator 14 is supported by a support 16 that, in the illustrated embodiment, comprises three legs 18 and a plate 20 connecting the three legs. However, the support may be differently configured while still supporting the load indicator in a desired positional relationship to the surface of the structure. The loading device 10 of the illustrated embodiment has two support hooks 22 protruding downward from the plate 20 that each engage a standoff 24 on opposed sides of the load indicator 14 such that the load indicator and connector 12 are supported by the support 16. However, the loading device could include a single support hook or three or more support hooks, if desired. The loading device 10 also comprises a load applicator in mechanical communication with the connector 12, the load indicator 14, and the structure for applying the load to the structure. Each of these elements of the present invention is more fully discussed hereafter.

As shown in FIG. 1, the composite structure 50 to be inspected defines protrusions 52 from the surface 54 of the structure. The protrusions 52 of the illustrated structure 50 are CLICKBOND fasteners that connect portions of the structure and that generally protrude above the surface 54 of the structure. The protrusions 52 preferably define a grippable portion, such as a threaded portion 56 of the protrusion shown in FIG. 1. The connector 12 of FIG. 1 may define a threaded orifice 26 that receives and threads onto the threaded portion 56 of the protrusion 52 to securely connect the connector to the protrusion. The connector of further embodiments of the present invention may comprise any means of connecting to the surface of the structure. FIG. 4 illustrates an alternative protrusion 152 that is removably adhered to the surface 154 of the structure 150. The connector 12 may be threaded onto the protrusion 152 to connect the connector to the surface 154 of the structure 150. Moreover, the connector 12 can engage the protrusion in a wide variety of manners other than a threaded engagement, if desired. Protrusions to which the connector 12 may be connected are discussed more fully hereafter.

Referring to FIGS. 1 and 2, the connector 12 is attached to the load indicator 14 with a load applicator 28. The load applicator 28, which is a turnbuckle in the illustrated embodiment of the loading device 10, is joined to the connector 12 and the load indicator 14 to adjust the distance between the connector and the load indicator, which applies the load to the surface 54 of the structure 50 through the connector. Load applicators 28 of further embodiments of the present invention may comprise any device that is in mechanical communication with the connector 12 and the load indicator 14, or with the load indicator and the structure 50, to apply a load on the surface 54 of the structure that is measurable by the load indicator. Advantageously, the load applicator 28 of the illustrated embodiment increases or decreases the distance between the connector 12 and the load indicator 14 in order to correspondingly decrease or increase the load on the structure, respectively. Non-limiting examples of alternative load applicators include pulley devices, jack-like devices, ratcheted devices, or toggling devices. In addition, the load applicator 28 may comprise an electromechanical device to adjust the distance between the connector 12 and the load indicator 14 such that the loading device 10 may be automated or remotely controlled for loading purposes in further alternative embodiments.

Referring again to the particular load applicator 28 of the illustrated embodiment, the turnbuckle preferably defines a top threaded orifice 30 that is threaded either directly or indirectly to a load-sensing portion 32 of the load indicator 14. In the illustrated embodiment, a hook 34 is threaded into the top threaded orifice 30 of the turnbuckle and hooked onto a similar hook-shaped portion of the load-sensing portion 32. Further embodiments of the present invention comprise alternative means of joining the turnbuckle to the load-sensing portion 32.

The turnbuckle also defines a bottom threaded orifice 40 that is threaded either directly or indirectly to the connector 12. The connector 12 of FIGS. 1 and 2 comprises a threaded portion 42 opposite the orifice 26, wherein the threaded portion is threaded into the bottom threaded orifice 40 of the turnbuckle. The threaded portion 42 of the connector 12 and the threads of the hook 34 are of a sufficient length to allow the distance between the connector and the load indicator 14 to be increased or decreased a distance that corresponds to the load required to be exerted by the loading device 10. The illustrated loading device 10 preferably applies a normal load of 75 pounds by rotating the turnbuckle relative to the connector 12 and the hook 34 to decrease the distance between the connector and the load indicator 14 until the load indicator displays 75 pounds of tension. Alternative embodiments of the loading device may apply a load greater or less than 75 pounds or may apply a compressive load of any magnitude. To apply a compressive load, the turnbuckle and/or the load applicator 28, are more rigidly joined to the load indicator 14 and the load indicator is more rigidly supported by the support 16 to withstand and measure the compressive loads applied by the turnbuckle or alternative load applicators. For each embodiment of the present invention, the load indicator 14 should sufficiently measure the entire range of loads the loading device 10 may apply.

To apply a normal load in tension as illustrated in FIGS. 1 and 2, the turnbuckle is rotated either by hand or with a handtool, such as a wrench or screwdriver to list two non-limiting examples. The threads of the threaded orifices 30 and 40 and the threads of the hook 34 and threaded portion 42, respectively, are oriented such that angular rotation of the turnbuckle in a first direction decreases the distance between the connector 12 and the load indicator 14 while angular rotation of the turnbuckle in an opposite direction increases the distance between the connector and load indicator. This decrease and increase in distances is preferably accomplished by providing standard right-hand threads on one combination of orifice and threaded rod, such as the top threaded orifice 30 and hook 34, while providing reverse threads on the other combination of orifice and threaded rod, such as the bottom threaded orifice 40 and threaded portion 42. These thread patterns may be reversed in alternative embodiments. Load applicators 28 of alternative embodiments of the present invention may apply the load by increasing or decreasing the distance between the connector 12 and the load indicator 14 by alternative means.

The load indicator 14 of FIGS. 1 and 2 can measure and indicate loads that are either in a compression direction and a tension direction. Load indicators of further embodiments of the present invention may measure and indicate loads in either a compression direction or a tension direction, as required by the respective application of the load indicator. The load indicator 14 detects the load through the load-sensing portion 32 and measures the load with mechanical devices to indicate the load on a display of the load indicator. The load indicator 14 of the illustrated embodiment comprises a dial, wherein the load is indicated by the angular position of a rotatable needle of the dial. Alternative load indicators of the present invention comprise electrical devices, such as load cells with strain gauges, that create a digital signal that can be processed and illustrated on a display, such as an LED display to name one non-limiting example. Further embodiments of the loading device may comprise load indicators that measure the loads by other means with or without a display or may comprise no load indicator and simply provide a predetermined load that the loading device is calibrated to apply. An example of a loading device having no load indicator comprises a loading device with a turnbuckle as previously discussed, wherein the rods that are threaded into the threaded orifices of the turnbuckle end at a position that corresponds to the desired loading. Further examples may also comprise load stops that create an internal engagement in the loading device to prevent the movement of the connector and load indicator beyond a predetermined distance that corresponds to the predetermined load.

The load indicator 14 of FIGS. 1 and 2 comprises standoffs 24 that project generally perpendicular to the display of the load indicator and generally perpendicular to the normal load that is measured. A first standoff 24 projects from a side of the load indicator 14 and a second standoff 24 projects from an opposite side of the load indicator. The standoffs 24 project in directions that are generally parallel to the plate 20 from which the support hooks 22 protrude. The standoffs 24 are positioned in the support hooks 22 to engage the support hooks such that the load indicator 14 is supported by the support 16. However, further embodiments of the present invention may support the load indicator by different means, such as threading a portion of the load indicator into the plate, to name one non-limiting example. Such further embodiments are advantageously used when the loading device applies a compressive load.

The plate 20 of FIGS. 1 and 2 is a generally planar plate of steel from which the support hooks 22 protrude and defines threaded holes through which the legs 18 pass. Further embodiments of the loading device may comprise a plate of any geometric shape, thickness, or material, or the loading device may not comprise a plate, such that the load indicator 14 is supported by the legs 18 by alternative means. The support 16 advantageously comprises a counterbalance eye (not shown), which may be attached to the plate 20 or legs 18 to facilitate movement of the loading device 10 or positioning of the loading device on non-horizontal surfaces. Straps or other supports from a crane or other lift device are advantageously passed through the counterbalance eye so that the loading device 10 may be conveniently lifted and positioned, particularly when the load is to be applied to a non-horizontal surface.

The legs 18 of the support 16 shown in FIGS. 1 and 2 are threaded rods that are threaded through the holes of the plate 20. Therefore, the legs 18 define adjustable lengths relative to the surface 54 of the structure 50 that the legs contact. Thus, the loading device 10 may be attached to surfaces that are not flat, such as angled, stepped, or otherwise non-planar surfaces, and still provide a normal load that is generally perpendicular to the surface 54 being inspected. Alternatively, the length of the legs 18 may be adjusted to accommodate loads to the surface 54 that are not generally perpendicular, for situations where non-normal loads may be required. The legs 18 are preferably long enough to provide sufficient clearance between the surface 54 and the plate 20 for the connector 12, the load applicator 28, the load indicator 14, and any attachments therebetween. The legs 18 are advantageously located apart from where the connector 12 will connect to the surface 54 of the structure 50 to provide convenient access to the surface of the structure proximate the location where the load is applied. The legs 18 contact a surface 54 of the structure 50 proximate the area of the structure to be inspected, but are advantageously located a sufficient distance away from where the load is applied so that the conteracting loads in the legs generally have a minimal effect on the load experienced in the inspected area of the structure. The loading device 10 of the illustrated embodiment defines a distance between the applied load and the legs 18 of approximately six inches; however, further embodiments may define a distance greater or less than six inches.

The legs 18 of the illustrated support 16 also comprise protective feet 44 at the end of the legs that contact the structure 50. The protective feet 44 protect the surface 54 of the structure 50 from being damaged when the loading device 10 is positioned on the structure and when loads counteracting the load are exerted on the surface of the structure through the legs when the load is applied. The protective feet 44 are threaded or adhered to the ends of the legs 18 opposite the plate and are preferably an elastomeric material; however, further embodiments may comprise feet that comprise other relatively soft or padded materials such as polymers, to list a non-limiting example. Still further embodiments of the loading device that apply a compressive load on the surface of the structure may comprise feet that contact the structure to withstand the counteracting load in tension.

To apply the normal load with the loading device 10 of FIGS. 1 and 2, the support is positioned on the surface 54 of the structure 50 such that the legs of the support contact the surface. The support 16 is preferably centered over the protrusion 52 to which the connector 12 is or shall be connected. Once the support 16 contacts the surface 54 and the plate 20 has been leveled to be generally perpendicular to the protrusion 52, or generally parallel to the surface of the structure, the connector 12 is connected to the protrusion. Alternatively, the connector 12 is connected to the protrusion 52 prior to the support 16 contacting the surface proximate the protrusion. After the turnbuckle and hook 34 are attached to the connector 12, the load indicator 14 is attached to the hook 34 and the support hooks 22 to completely assembly the loading device 10. Once the loading device 10 is substantially assembled, the turnbuckle is rotated to decrease the distance between the connector 12 and the load indicator 14 until a predetermined normal load is exerted on the protrusion 52. Once the predetermined load, such as the 75 pound load mentioned above, is exerted on the protrusion 52, the rotation of the turnbuckle is stopped. The loading device 10, may indefinitely maintain the load applied to the structure 50 so that the technician performing the nondestructive inspection has sufficient time to inspect the structure proximate the loading device. Loading devices of alternative embodiments may require different assembly and loading techniques. In addition, the steps for applying the load may be performed in any reasonable sequence based upon the structure of the loading device or the convenience of the technician using the loading device.

FIG. 3 illustrates the connector 12 threaded onto the surface 54 of the structure 50. The surface 54 defines a protrusion 52 that comprises a threaded portion 56. The protrusion 52 may be a permanent feature of the structure 50 such as CLICKBOND fasteners used in nacelle sandwich panels, to list one non-limiting example, or may be a temporary feature of the structure as shown in FIG. 4. Referring again to FIG. 3, the connector 12 defines a threaded orifice 26. The threaded orifice 26 is advantageously located in the center of the connector 12 so that the connector may be conveniently threaded onto the protrusion 52 either before or after the connector is attached to the load indicator 14. The threaded orifice 26 advantageously defines a thread pattern that corresponds with the thread pattern of the threaded portion 56 of the protrusion 52. The connector 12 is advantageously threaded onto a sufficient number of threads of the protrusion 52 to withstand the load without damaging the threads or causing the connector to disconnect from the protrusion. Alternative structures may define features of the surface to which the connector 12, or connectors of further embodiments of the loading device, may connect. In addition, a threaded protrusion may be removably adhered to the surface of the structure for connection with the connector.

FIG. 4 illustrates a protrusion 152 that is removably adhered to a surface 154 of the structure 150. The protrusion 152 has a threaded portion 156 opposite a surface that is removably adhered to the surface 154 of the structure 150. A removable adhesive 158 is applied between the protrusion 152 and the surface 154 so that when the protrusion contacts the surface the protrusion is adhered to the surface. The adhesive may be applied directly to the surface 154 or the protrusion 152, and is preferably an adhesive that sets relatively quickly at room temperature. Adhesives having the generic vendor name EA9394 is a non-limiting example of a removable adhesive 158 that is advantageously used with the protrusion 152. To improve the adhesion between the protrusion 152 and the surface 150, the surface 154 may be lightly abraded and cleaned prior to the adhesive 158 contacting the surface. The adhesive 158 must provide an adhesive strength sufficient to withstand the predetermined load in tension. To remove the adhesive 158, which is advantageously a temperature sensitive adhesive, heat is applied to the adhesive 158 until the bond created by the adhesive is sufficiently weakened so the protrusion may be removed and the adhesive cleaned off the structure 150. Alternatively, the adhesive 158 may be scraped away or exposed to a solvent that weakens the bond strength of the adhesive, or the protrusion 152 may be moved in a direction that the adhesive has minimal bond strength, such as in a rotational direction, to describe a three non-limiting examples of methods to remove the adhered protrusion. Once the protrusion 152 has been removed, the surface 154 may be cleaned to return the structure 150 to its pre-inspection condition.

The loading device of the present invention applies a load to a surface of a composite structure undergoing a non-destructive inspection to accentuate internal defects in the structure. The load may cause weak bonds that would normally be undetected to fail such that the inspection will detect the disbond, or it may reveal disbonds between composite plies that contact one another when experiencing no load but that also readily separate once loaded. The non-destructive inspection advantageously incorporates traditional pulse-echo or through transmission ultrasonic techniques to detect disbonds or defects in the area of the structure being inspected. Further non-destructive inspection techniques may also be used with the loading device of the present invention. The ultrasonic inspection device, or other non-destructive inspection device, preferably produces a signal that may be processed by a processing element to produce a visual display, such as a graphic or numeric illustration, that the technician performing the inspection can monitor for indications of a disbond or defect. The processed signal may also be recorded for subsequent analysis of the inspection results. Any detected disbonds or defects requiring remediation may be repaired, or if necessary, the structure may be replaced.

The loading device of the present invention may be conveniently assembled on a surface of a structure and is compatible with surfaces at various orientations or having various surface features. In addition, the loading device provides convenient access to the surface of the structure proximate the location where the load is applied so that the non-destructive inspection may be conveniently performed. Furthermore, the loading device may be used on surfaces with or without protrusions. Accordingly, the loading device provides a load that can be conveniently applied to a surface of a composite structure for non-destructive inspection purposes.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Which is claimed is:

1. A loading device for applying a load to a surface of a composite structure during a non-destructive inspection of an area of the structure, the loading device comprising:
   a load indicator to indicate the load applied to the structure;
   a connector for connecting the load indicator to the surface of the structure being inspected;
   a load applicator in mechanical communication with the connector and the load indicator for applying the load to the structure; and
   a support for supporting the load indicator and connector, wherein the support contacts a surface of the structure proximate the area of the structure to be inspected, wherein the connector defines a threaded orifice for threading directly onto the surface of the structure.

2. A loading device according to claim 1 wherein the support comprises three legs and a plate connecting the three legs, wherein an end of each leg opposite the plate contacts the surface of the structure and wherein the load indicator is attached to the plate.

3. A loading device according to claim 2 wherein each end of the legs opposite the plate comprises a protective end for contacting the surface of the structure.

4. A loading device according to claim 2 wherein the load indicator comprises a first standoff on a side of the load indicator and a second standoff on an opposite side of the load indicator and wherein two support hooks protrude from the plate of the support such that each standoff engages a support hook to support the load indicator and the connector.

5. A loading device according to claim 2 wherein the legs define an adjustable length so that the loading device is capable of applying the load while contacting a non-planar surface of the structure.

6. A loading device according to claim 1 wherein the load applicator comprises a turnbuckle that attaches the connector to the load indicator, wherein the load is applied by rotating the turnbuckle to create tension between the connector and the load indicator.

7. A loading device according to claim 1 wherein the load indicator comprises a dial for indicating the load.

8. A loading device according to claim 1 wherein a protrusion is removably adhered to the surface of the structure and the connector is connected to the protrusion.

9. A loading device for applying a load to a surface of a composite structure during a non-destructive inspection of an area of the structure, the loading device comprising:
   a load indicator to indicate the load applied to the structure;
   a load applicator in mechanical communication with the load indicator and the structure for applying the load to the structure; and
   a support for supporting the load indicator and the load applicator, wherein the support contacts the surface of the structure proximate the area of the structure to be inspected, the support comprising:
      a plate, wherein the load indicator is attached to the plate; and
      at least three legs defining an adjustable length connected by the plate for contacting the surface of the structure; and,
      a connector for connecting the load indicator to the surface of the structure being inspected, wherein the connector is in mechanical communication with the load applicator, the load indicator, and the surface of the structure; wherein the connector defines a threaded orifice for threading directly onto the surface of the structure.

10. A loading device according to claim 9 wherein the load applicator comprises a turnbuckle that attaches the connector to the load indicator, wherein the load is applied by rotating the turnbuckle to create tension between the connector and the load indicator.

11. A loading device according to claim 9 wherein a protrusion is removably adhered to the surface of the structure and the connector is connected to the protrusion.

12. A loading device according to claim 9 wherein each end of the legs opposite the plate comprises a protective end for contacting the surface of the structure.

13. A loading device according to claim 9 wherein the load indicator comprises a first standoff on a side of the load indicator and a second standoff on an opposite side of the load indicator and wherein two support hooks protrude from the plate of the support such that each standoff engages a support hook to support the load indicator and the load applicator.

14. A method of applying a load to a surface of a composite structure during a non-destructive inspection of an area of the structure, the method comprising the steps of:
   positioning a support on the surface of the structure such that the support contacts the surface proximate the area of the structure to be inspected;
   connecting a connector to the surface of the structure;
   attaching the connector to a load indicator that indicates the load and that is supported by the support; and
   adjusting a distance between the connector and the load indicator to apply the load to the surface of the structure, wherein connecting the connector comprises threading the connector directly onto the surface of the structure.

15. A method according to claim 14 wherein adjusting the distance between the connector and the load indicator comprises rotating a turnbuckle.

16. A method according to claim 14 wherein positioning the support comprises the adjusting of a length of one or more legs of the support.

17. A method according to claim 14, further comprising the step of adhering a protrusion to the surface of the structure such that the connecting a connector to the surface of the structure comprises connecting the connector to the adhered protrusion.

18. A method according to claim 14, further comprising the step of performing a non-destructive inspection of the area of the structure.

* * * * *